(12) United States Patent
Dalene et al.

(10) Patent No.: US 9,888,873 B2
(45) Date of Patent: *Feb. 13, 2018

(54) NIRS SENSOR ASSEMBLY INCLUDING EMI SHIELDING

(71) Applicant: CAS Medical Systems, Inc., Branford, CT (US)

(72) Inventors: Matthew Dalene, Clinton, CT (US); Karen Duffy, Orange, CT (US); John Gamelin, Avon, CT (US); Paul Benni, Acton, MA (US); William Kosturko, Milford, CT (US)

(73) Assignee: CAS Medical Systems, Inc., Branford, CT (US)

( * ) Notice: Subject to any disclaimer, the term of this patent is extended or adjusted under 35 U.S.C. 154(b) by 240 days.

This patent is subject to a terminal disclaimer.

(21) Appl. No.: 14/102,004

(22) Filed: Dec. 10, 2013

(65) Prior Publication Data

US 2014/0171761 A1    Jun. 19, 2014

Related U.S. Application Data

(60) Provisional application No. 61/735,318, filed on Dec. 10, 2012.

(51) Int. Cl.
*A61B 5/1455*    (2006.01)
*A61B 5/00*    (2006.01)

(52) U.S. Cl.
CPC ........ *A61B 5/14552* (2013.01); *A61B 5/6832* (2013.01); *A61B 2562/182* (2013.01); *A61B 2562/222* (2013.01)

(58) Field of Classification Search
None
See application file for complete search history.

(56) References Cited

U.S. PATENT DOCUMENTS

| 5,094,240 A | * | 3/1992 | Muz | A61B 5/14552 600/324 |
|---|---|---|---|---|
| 8,188,433 B2 | | 5/2012 | Gonopolskiy et al. | |
| 2002/0016536 A1 | * | 2/2002 | Benni | A61B 5/14552 600/323 |
| 2013/0012822 A1 | * | 1/2013 | Kosturko | A61B 5/1455 600/476 |

\* cited by examiner

*Primary Examiner* — Eric Winakur
*Assistant Examiner* — Marjan Fardanesh
(74) *Attorney, Agent, or Firm* — O'Shea Getz P.C.

(57) ABSTRACT

A NIRS sensor assembly includes a light source, a light detector, a first insulating layer, an EMI shielding layer, and a second insulating layer. The first insulating layer covers an exposed portion of the light detector. An optically transparent portion of the first insulating layer is aligned with an active area of the light detector. The EMI shielding layer covers the first insulating layer. An optically transparent portion of the EMI shielding layer is aligned with the active area of the light detector. The second insulating layer covers the EMI shielding layer and the first insulating layer. An optically transparent portion of the second insulating layer is aligned with the active area of the at least one light detector.

16 Claims, 8 Drawing Sheets

NIRS SENSOR ASSEMBLY INCLUDING EMI SHIELDING

This application claims priority to U.S. Patent Appln. No. 61/735,318 filed Dec. 10, 2012.

BACKGROUND OF THE INVENTION

1. Technical Field

This invention relates to near-infrared spectroscopy (NIRS) sensor assemblies in general, and to NIRS sensor assemblies that include electromagnetic interference (EMI) shielding in particular.

2. Background Information

NIRS sensor assemblies are commonly used to non-invasively measure a characteristic (e.g., blood oxygenation) of a biological tissue. A problem common to NIRS sensor assemblies is signal interference (e.g., EMI) from external sources. Another problem common to NIRS sensor assemblies is signal interference (e.g., EMI) from internal sources (e.g., from light sources and/or light detectors included in the NIRS sensor assemblies). Another problem common to NIRS sensor assemblies is the cost to manufacture. Aspects of the present invention are directed to these and other problems.

SUMMARY OF THE INVENTION

According to an aspect of the present invention, a NIRS sensor assembly for non-invasively measuring a characteristic of a biological tissue is provided. The NIRS sensor assembly includes at least one light source, at least one light detector, a first insulating layer, an EMI shielding layer, and a second insulating layer. The light source is operable to emit light signals. The detector is operable to detect light signals, and includes an active area through which light signals may be detected. The first insulating layer is disposed relative to the light detector in a manner that covers a portion of the detector. The first insulating layer is electrically non-conductive. An optically transparent portion of the first insulating layer is aligned with the active area of the detector. The EMI shielding layer is disposed in contact with the first insulation layer in a manner that covers the first insulating layer. The EMI shielding layer is electrically conductive. An optically transparent portion of the EMI shielding layer is aligned with the active area of the detector. The second insulating layer is disposed in contact with the EMI shielding layer in a manner that covers the EMI shielding layer and the first insulating layer. The second insulating layer is electrically non-conductive. An optically transparent portion of the second insulating layer is aligned with the active area of the light detector.

According to another aspect of the present invention, a NIRS sensor assembly for non-invasively measuring a characteristic of a biological tissue is provided. The NIRS sensor assembly includes a flexible circuit, a light source, a light detector, a connector, a first insulating layer, an EMI shielding layer, a second insulating layer, and a pad. The light source is in electrical communication with the flexible circuit. The light source is operable to emit light signals. The light detector is in electrical communication with the flexible circuit, and has an active area for detecting light signals emitted by the light source and passed through the subject's body tissue. The connector is in electrical communication with the flexible circuit. The first insulating layer is disposed relative to the light detector, and is electrically non-conductive. The EMI shielding layer is disposed relative to the first insulating layer, and is electrically conductive. The second insulating layer is disposed relative to the first insulating layer and the EMI shielding layer. The second insulating layer is electrically non-conductive. The pad has a light source aperture and a light detector aperture. The light source is received at least partially within the light source aperture, and the light detector is at least partially received within the light detector aperture. The pad is positioned within the NIRS sensor assembly to contact a subject during operation of the NIRS sensor assembly.

According to another aspect of the present invention, a flexible circuit for use in a NIRS sensor assembly is provided. The flexible circuit is in electrical communication with at least one light source of the NIRS sensor assembly and at least one light detector of the NIRS sensor assembly. The flexible circuit includes a plurality of light source wires, a plurality of light detector wires, and EMI shielding. The plurality of light source wires are configured to communicate electrical signals between the at least one light source and a connector portion of the NIRS sensor assembly. The plurality of light detector wires are configured to communicate electrical signals between the at least one light detector and the connector portion. The EMI shielding is configured to reduce cross-talk between the plurality of light source wires and the plurality of light detector wires.

These and other features and advantages of the present invention will become apparent in light of the drawings and detailed description of the present invention provided below.

DETAILED DESCRIPTION OF THE INVENTION

Figure 1:
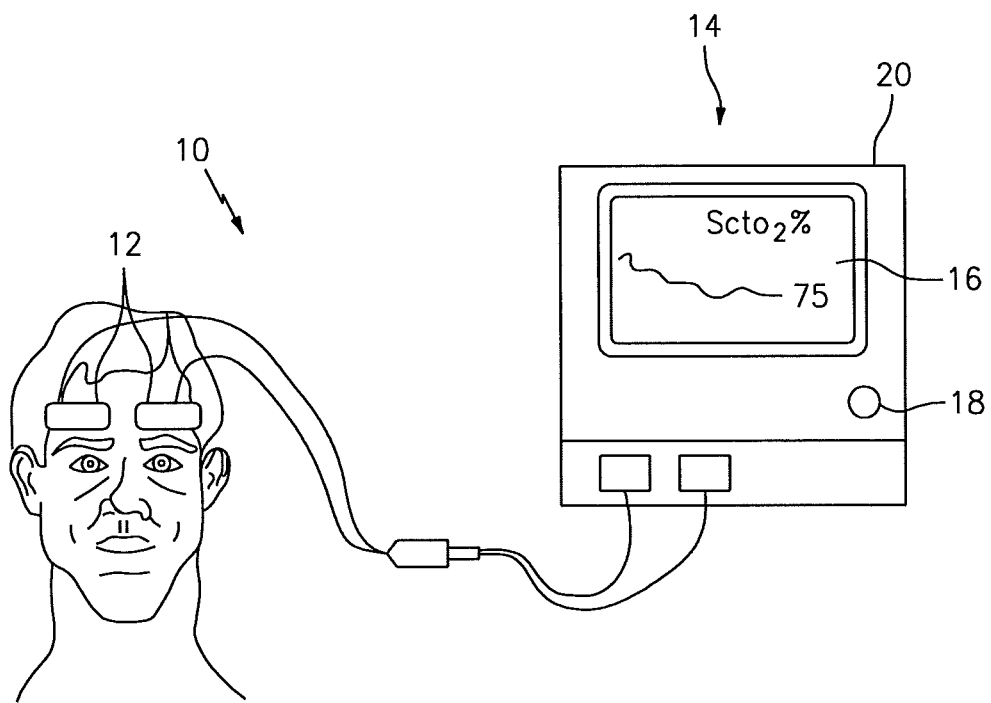
FIG. 1 is a diagrammatic view of a pair of NIRS sensor assemblies mounted on a patient and connected to a NIRS system.

Referring to FIG. 1, a NIRS system 10 includes one or more NIRS sensor assemblies 12 connected to a base unit 14. The base unit 14 includes a display 16, operator controls 18, and a processor 20 for providing signals to and/or receiving signals from the NIRS sensor assembly(ies) 12. The processor 20 is adapted (e.g., programmed) to selectively perform the functions necessary to operate the NIRS sensor assembly(ies) 12. It should be noted that the functionality of the processor 20 may be implemented using hardware, software, firmware, or a combination thereof. A person skilled in the art would be able to program the processor 20 to perform the functionality described herein without undue experimentation. For purposes of providing a detailed description of the present NIRS sensor assembly(ies) 12, the NIRS sensor assembly(ies) 12 will be described herein as being used in connection with a NIRS system 10 similar to the ones described in U.S. Pat. Nos. 6,456,862 and 7,072,701, each of which patents is hereby incorporated by reference in its entirety. The NIRS sensor assembly(ies) 12 is not, however, limited to use with any particular NIRS system 10.

FIGS. 2-8 illustrate an embodiment of the NIRS sensor assembly 12 shown in FIG. 1. The NIRS sensor assembly 12 includes a flexible electrical circuit 22, one or more light sources 24, one or more light detectors 26, 28, a first insulating layer 30, an EMI shielding layer 32, a second insulating layer 34, a third insulating layer 36, a pad 38, a cover 40, a tail cover 42, and a connector 44. The NIRS sensor assembly 12, and/or features of the NIRS sensor assembly 12, may be described as having a length extending along an x-axis, a width extending along a y-axis, and a thickness extending along a z-axis. FIGS. 2-8 illustrate the respective axes.

Figure 2:
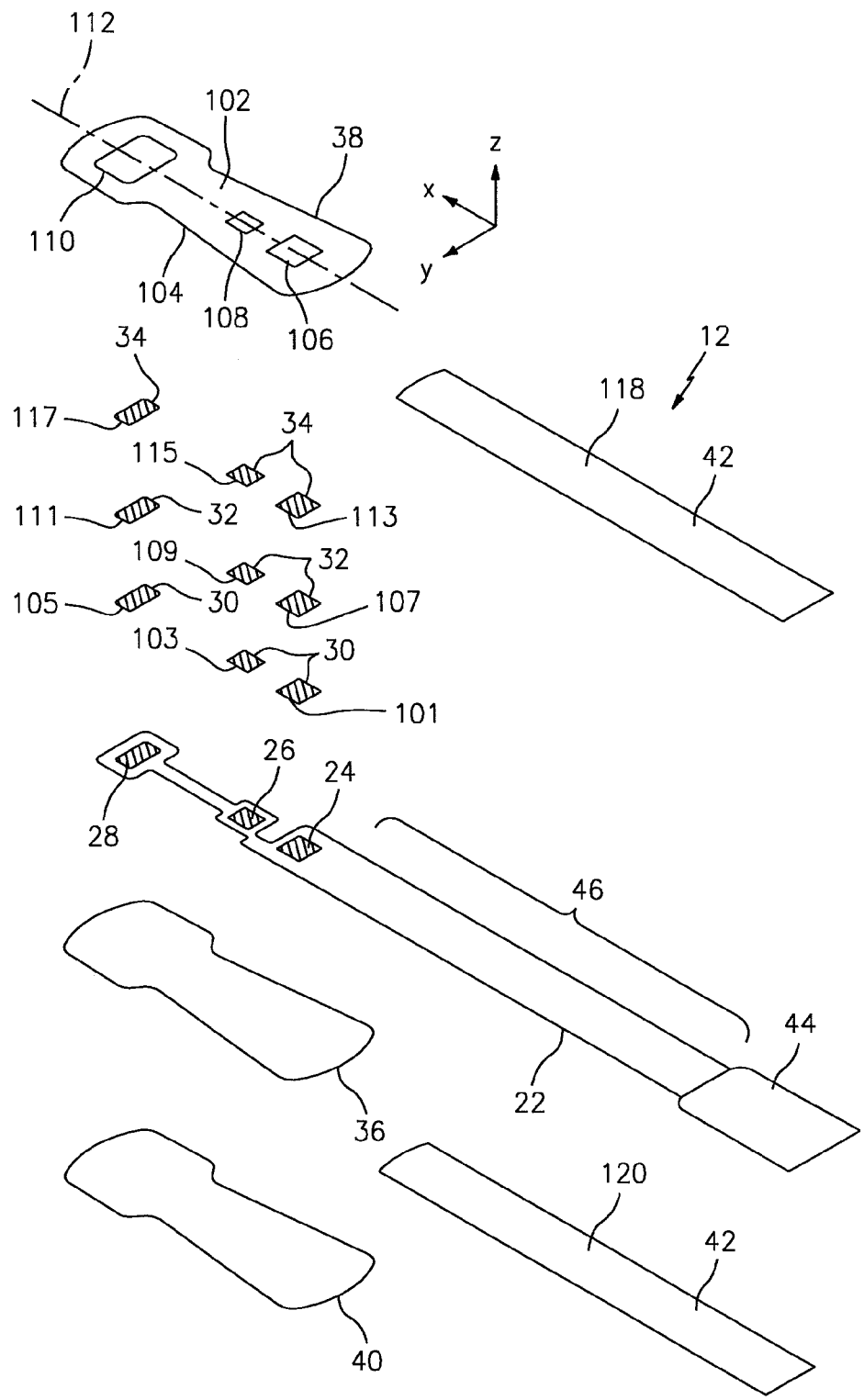
FIG. 2 is an exploded view of a NIRS sensor assembly embodiment.

Referring to FIG. 2, the light source 24 includes one or more light emitting components (e.g., light emitting diodes (LEDs), laser diodes, etc.) that are selectively operable to produce infrared light (i.e., light in wavelength range of about seven hundred nanometers (700 nm) to about one thousand nanometers (1,000 nm)) at one or more predetermined wavelengths. In other embodiments, the light source 24 may alternatively or additionally produce visible light (i.e., light in the wavelength range of about three hundred ninety nanometers (390 nm) to about seven hundred fifty nanometers (750 nm)). As will be described in detail below, the light source 24 is mounted on a flexible electrical circuit 22 (hereinafter referred to as a "flex circuit 22") for electrical communication with the base unit 14.

Each of the light detectors 26, 28 includes one or more light responsive transducers (e.g., photodiodes, charge-coupled devices etc.) that are operable to detect light emitted by the light source 24 after such light passes through a portion of the subject's body. Each of the light detectors 26, 28 includes an active region through which light can be detected. As will be described in detail below, each of the light detectors 26, 28 is mounted on the flex circuit 22 for electrical communication with the base unit 14. The light detector 26 closest to the light source 24 may be referred to hereinafter as the "near detector 26", and the light detector 28 farthest from the light source 24 may be referred to hereinafter as the "far detector 28".

The relative positioning of the light source 24 and the light detectors 26, 28 on the NIRS sensor assembly 12 can be varied for different applications. The NIRS sensor assembly 12 is not limited to any particular relative positioning of the light source 24 and the light detectors 26, 28. International Patent Application No. PCT/US12/24889, which is hereby incorporated by reference in its entirety, discloses several examples of acceptable light source/light detector relative positioning. The relative positioning of the light source 24 and the light detectors 26, 28 may, for example, be selected so that: (1) the light source 24 and the light detectors 26, 28 are substantially linearly aligned along a lengthwise-extending axis; and (2) the separation distances between the light source 24 and each of the light detectors 26, 28 are not the same.

Figure 9:
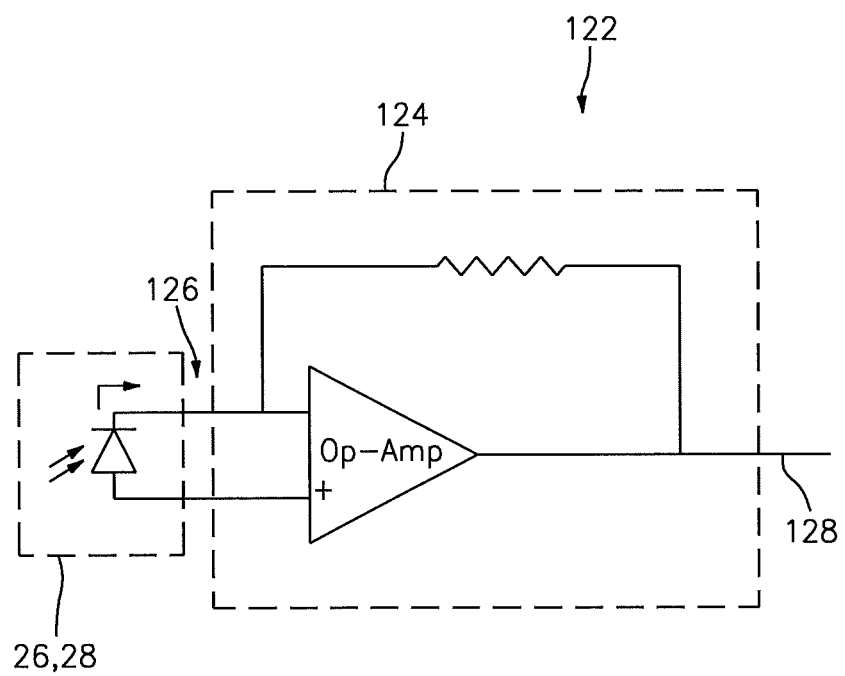
FIG. 9 is a circuit diagram showing a luminance measuring device.
Figure 10:
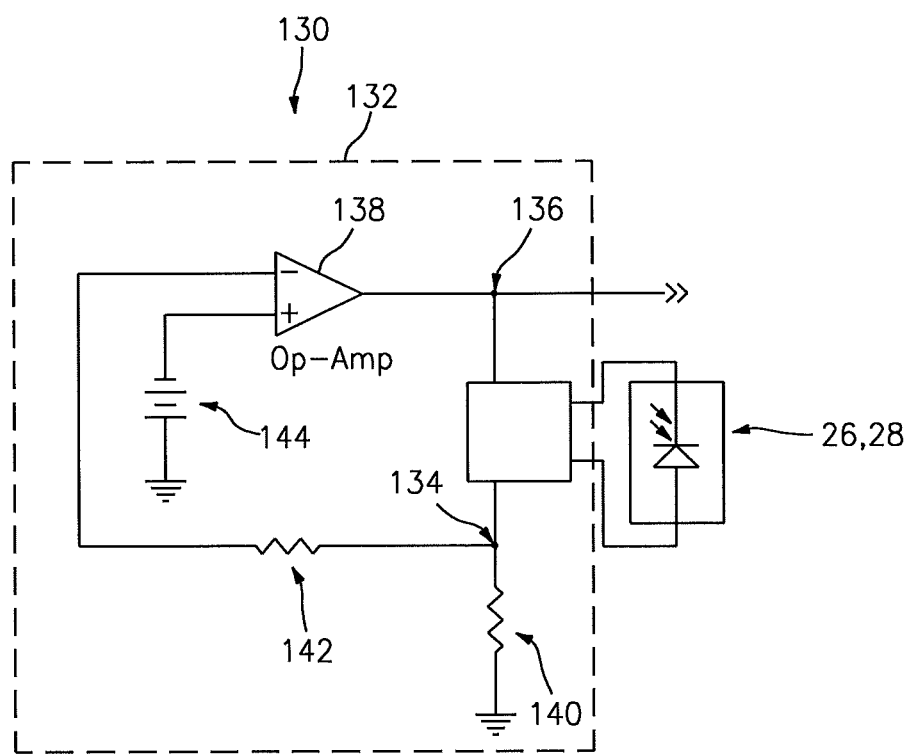
FIG. 10 is a circuit diagram showing a temperature measuring device.

The NIRS sensor assembly 12 may be configured so that one or more of the light detectors 26, 28 can be used in measuring the luminance and/or temperature of the light source 24. For example, in some embodiments, a light detector 26 may be positioned sufficiently close to the light source 24 so that: a) the luminance of light detected by the light detector 26 is indicative of the luminance of the light emitted by the light source 24; and b) the temperature of the light detector 26 is indicative of the temperature of the light source 24. In the embodiments wherein a detector 26 is used in the measurement of the luminance of the light source 24, the NIRS sensor assembly 12 may be used with a luminance measuring device. Examples of acceptable luminance measuring devices are disclosed in U.S. patent application Ser. No. 13/543,180 (published as U.S. Patent Publication no. 2013/0012822), which is hereby incorporated by reference in its entirety. FIG. 9 illustrates an example of a luminance measuring device 122 that includes a photovoltaic circuit 124 that is zero biased and has a zero ohm input impedance. The input 126 of the photovoltaic circuit 124 receives signals from the light detector 26. The output 128 of the photovoltaic circuit 124 provides signals relating to the luminance detected by the light detector 26, which signals may be transmitted to the base unit 14 (see FIG. 1) for processing. The processor 20 of the base unit 14 (see FIG. 1) may adjust an operational characteristic of the light source 24 (e.g., luminance of the light emitted by the light source) in response to the signals from the luminance measuring device 122. In the embodiments wherein a detector 26 is used in the measurement of the temperature of the light source 24, the NIRS sensor assembly 12 may be used with a temperature measuring device. Examples of acceptable temperature measuring devices are disclosed in U.S. patent application Ser. No. 13/543,180 (published as U.S. Patent Publication no. 2013/0012822). FIG. 10 illustrates an example of a temperature measuring device 130 that includes a circuit 132 for converting a signal received from the light detector 26 into a signal indicative of the temperature of the light detector 26. The circuit 132 biases the light detector 26 with a constant current. The circuit 132 includes an input 134, an output 136, an op-amp 138, a first load 140, a second load 142 and a voltage source 144. The input 134 receives the signal from the light detector 26. The output 136 of the circuit 132 provides a signal relating to the temperature of the light detector 26, which signal is transmitted to the base unit 14 (see FIG. 1) for processing. The processor 20 of the base unit 14 (see FIG. 1) may adjust an operational characteristic of the light source (e.g., luminance of the light emitted by the light source) in response to the signal from the temperature measuring device. The example provided above describes the near light detector 26 as the detector used in the measurement of the luminance and/or temperature of the light source 24. The present sensor is not limited to using the near detector 26 for these functions, and may, for example include a separate light detector dedicated to measuring the luminance and/or temperature of the light source 24.

Figure 3:
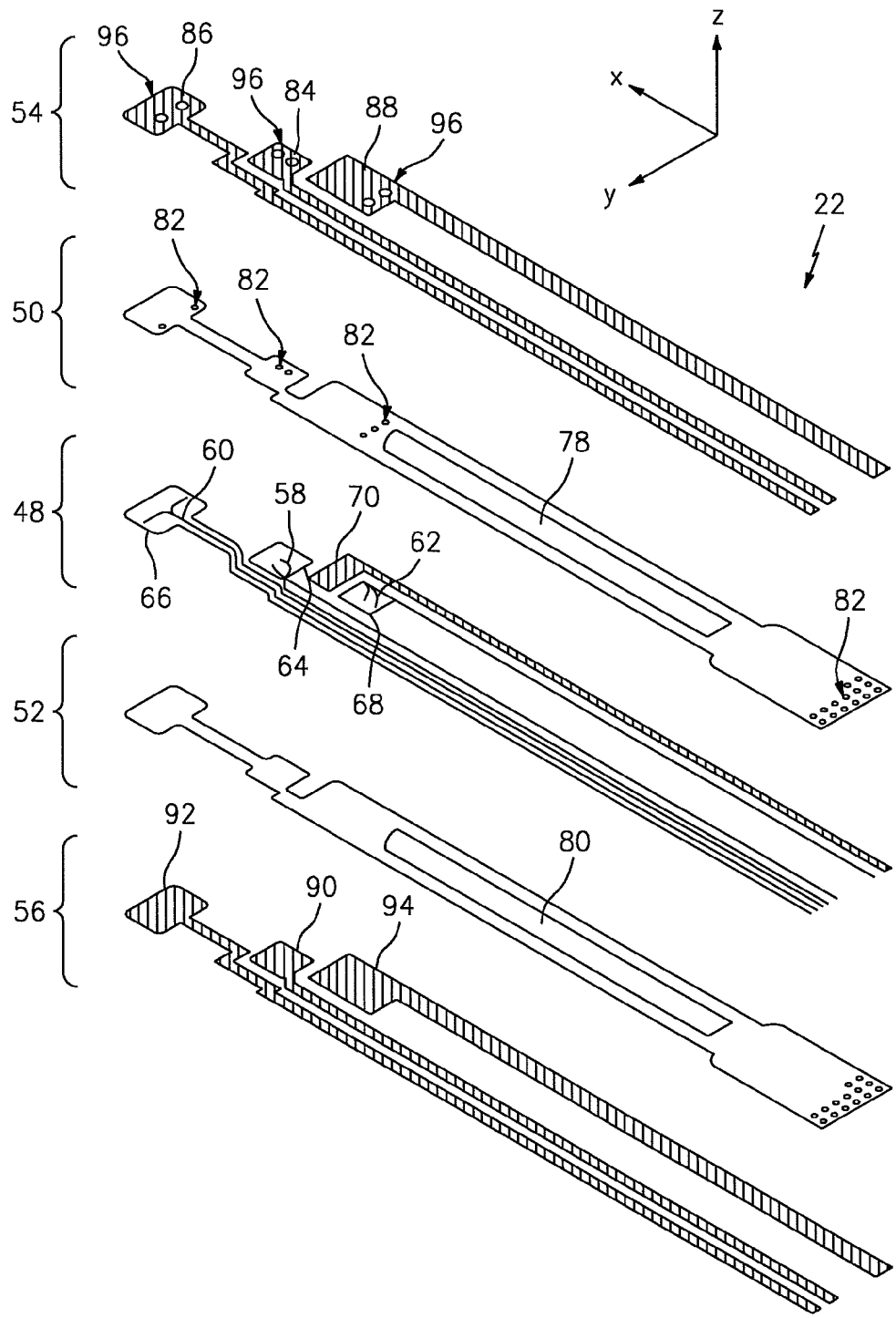
FIG. 3 is an exploded view of a flexible electrical circuit embodiment.

Referring to FIGS. 2 and 3, the flex circuit 22 electrically connects the light detectors 26, 28 and the light source 24 to the connector 44. The connector 44, in turn, provides the structure that allows the NIRS sensor assembly 12 to be electrically connected to the base unit 14 (see FIG. 1). In FIG. 2, the flex circuit 22 is configured so that the far detector 28 is positioned proximate one end of the flex circuit 22, and the near detector 26 is spaced apart from the far detector 28 and is disposed between the far detector 28 and the light source 24. Adjacent the light source 24, a tail portion 46 of the flex circuit 22 extends outwardly, terminating at the connector 44.

The flex circuit 22 may include a plurality of layers. In the embodiment illustrated in FIG. 3, the flex circuit 22 includes five (5) layers: a communication layer 48, a pad-side insulating layer 50, a cover-side insulating layer 52, a pad-side shielding layer 54, and a cover-side shielding layer 56. The several layers of the flex circuit 22 are laminated, bonded, or otherwise attached together to form a single structure, as shown for example in FIGS. 7 and 8, which are discussed below. Acceptable materials for laminating, bonding, or attaching layers of the flex circuit 22 together are known in the art and will not be discussed herein. The flex circuit 22 embodiment illustrated in FIGS. 3-7 is for illustrative purposes only; aspects of the present invention may be used with a variety of different flex circuit 22 embodiments. For example, other embodiments of the flex circuit 22 may have more layers or fewer layers than the embodiment illustrated in FIGS. 3-7.

In the embodiment illustrated in FIG. 3, the communication layer 48 includes a plurality of near detector wires 58, a plurality of far detector wires 60, and a plurality of light source wires 62. The wires 58, 60, 62 are made of a metal (e.g., copper), or a conductive polymer, or any other known material operable to conduct electrical signals. The term "wire" is used herein to describe an electrically conductive member, and is not limited to any particular structure. The near detector wires 58 are configured to communicate electrical signals between the near detector 26 and the connector 44. The far detector wires 60 are configured to communicate electrical signals between the far detector 28 and the connector 44. The exact number of near detector wires 58 and far detector wires 60 may vary; e.g., depending on whether the near detector 26 and far detector 28 each include one photodiode or a plurality of photodiodes. The light source wires 62 are configured to communicate electrical signals between the light source 24 and the connector 44. The exact number of light source wires 62 may vary; e.g., depending on whether the light source 24 includes one LED or a plurality of LEDs.

Referring to FIG. 3, the communication layer 48 includes one or more EMI shielding wires 64 disposed relative to the near detector wires 58, one or more EMI shielding wires 66 disposed relative to the far detector wires 60, and one or more EMI shielding wires 68 disposed relative to the light source wires 62. The communication layer 48 also includes one or more EMI shielding sheets 70. The term "sheet" is used herein to refer to a structure having planar dimensions (i.e., dimensions in the x-y plane) that are substantially greater than a thickness dimension (i.e., a dimension along the z-axis). The EMI shielding wires 64, 66, 68 and EMI shielding sheet 70 may generally be referred to herein as "EMI shielding". The EMI shielding wires 64, 66, 68 and the EMI shielding sheet 70 are preferably directly or indirectly connected to ground, but not necessarily. The EMI shielding wires 64, 66, 68 and the EMI shielding sheet 70 may at least partially form one or more Faraday cages around one or more of the wires 58, 60, 62, as will be discussed below. The EMI shielding wires 64, 66, 68 and the EMI shielding sheet 70 may be made from the same or similar material as the wires 58, 60, 62, or any other material operable to shield against EMI.

Figure 4:
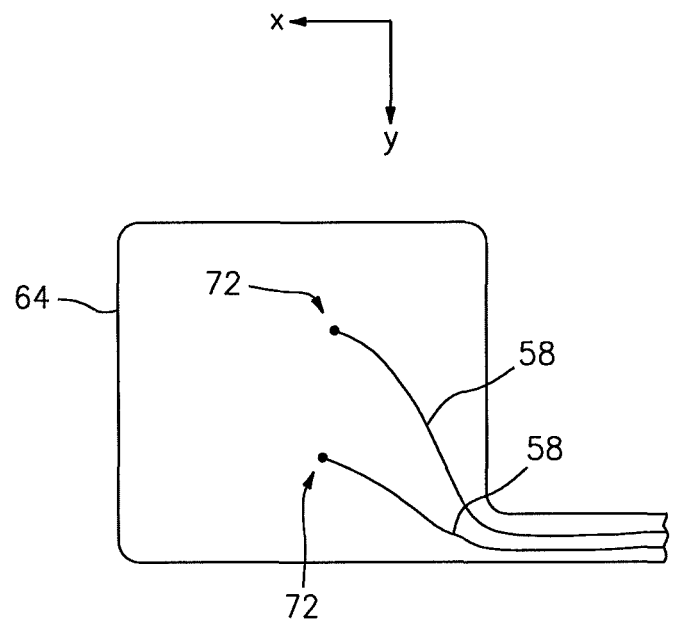
FIG. 4 is a planar view of a portion of the communication layer of the flexible electrical circuit embodiment illustrated in FIG. 3.

FIG. 4 illustrates the near detector wires 58 shown in FIG. 3. Each of the near detector wires 58 includes an end portion 72 that may be electrically connected (e.g., by soldering) to the near detector 26. As shown in FIG. 4, EMI shielding wire 64 runs substantially parallel to the near detector wires 58 and circumscribes the end portions 72 of the near detector wires 58. The EMI shielding wire 64 is preferably directly or indirectly connected to ground, and aids in shielding the near detector wires 58 against EMI. EMI may be generated from any one of a number of sources (e.g., sources within the NIRS sensor assembly 12, or external sources). For example, electrical currents passing through the light source wires 62 (see FIG. 6, discussed below) may generate EMI proximate the end portions 74 of the light source wires 62. Accordingly, the EMI shielding wire 64 may be oriented relative to the end portions 72 of the near detector wires 58 so that they (the end portions 72) are shielded from EMI generated proximate the end portions 74 of the light source wires 62. The near detector wires 58 and the EMI shielding wire 64 are not limited to the embodiment illustrated in FIGS. 3 and 4.

Figure 5:
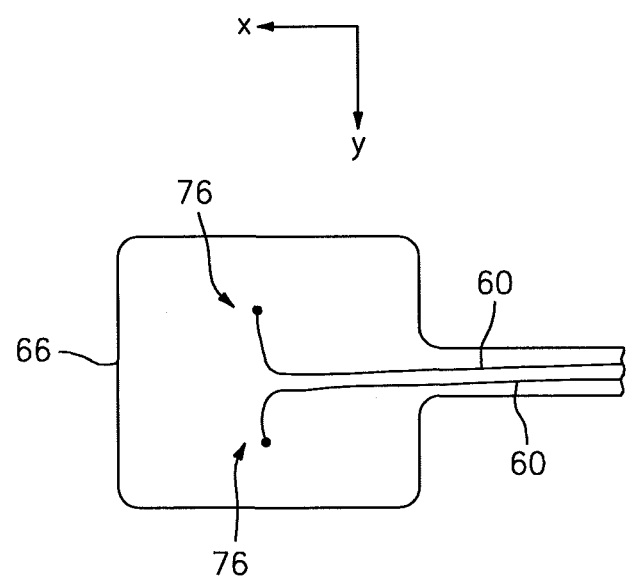
FIG. 5 is a planar view of a portion of the communication layer of the flexible electrical circuit embodiment illustrated in FIG. 3.

FIG. 5 illustrates the far detector wires 60 shown in FIG. 3. The far detector wires 60 are configured similar to the near detector wires 58; e.g., each includes an end portion 76 that may be electrically connected (e.g., by soldering) to the far light detector 28. As shown in FIG. 5, EMI shielding wire 66 runs substantially parallel to the far detector wires 60 and circumscribes the end portions 76 of the far detector wires 60. The EMI shielding wire 66 is preferably directly or indirectly connected to ground, and shields the far detector wires 60 against EMI. As indicated above, EMI may be may be generated from any one of a number of sources. For example, electrical currents passing through the light source wires 62 (see FIG. 6, discussed below) may generate EMI proximate the end portions 74 of the light source wires 62. Accordingly, the EMI shielding wire 66 may be oriented relative to the end portions 76 of the far detector wires 60 so that they (the end portions 60) are shielded from EMI generated proximate the end portions 74 of the light source wires 62. The far detector wires 60 and the EMI shielding wire 66 are not limited to the embodiment illustrated in FIGS. 3 and 5.

Figure 6:
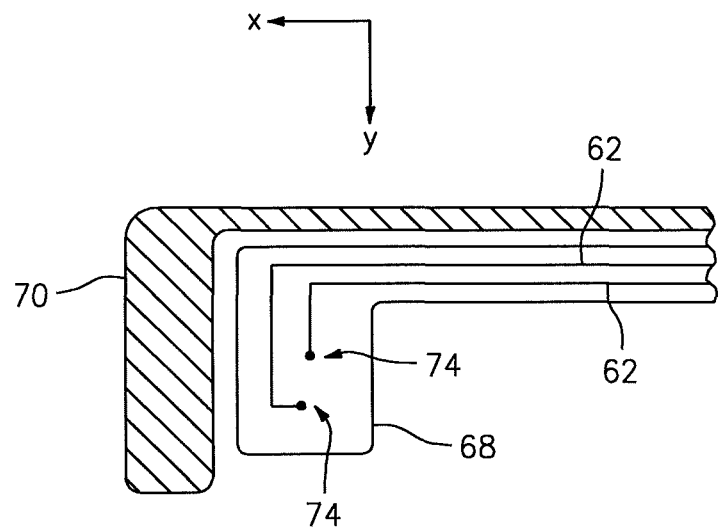
FIG. 6 is a planar view of a portion of the communication layer of the flexible electrical circuit embodiment illustrated in FIG. 3.

FIG. 6 illustrates the light source wires 62 shown in FIG. 3. Each of the light source wires 62 includes an end portion 74 that may be electrically connected (e.g., by soldering) to the light source 24. As shown in FIG. 6, an EMI shielding wire 68 runs substantially parallel to the light source wires 62 and circumscribes the end portions 74 of the light source wires 62. The communication layer 48 of the flex circuit 22 additionally includes an EMI shielding sheet 70 disposed proximate the light source wires 62, and between the light source wires 62 and the near detector wires 58 and the far detector wires 60. The EMI shielding sheet 70 reduces or prevents EMI generated at the end portions 74 of the light source wires 62 from being received by the end portions 72 of the near detector wires 58 and the end portions 76 of the far detector wires 60. The transmission of EMI between the near detector wires 58, the far detector wires 60, and the light source wires 62 may be referred to hereinafter as "cross-talk". The EMI shielding wires 64, 66, 68 and EMI shielding sheet 70 are operable to reduce or prevent cross-talk between the near detector wires 58, the far detector wires 60, and the light source wires 62.

Referring to FIG. 3, the pad-side insulating layer 50 and the cover-side insulating layer 52 each have a geometry that generally matches the communication layer 48 of the flex circuit 22. The pad-side insulating layer 50 and the cover-side insulating layer 52 are proximate (though not necessarily in contact with) the pad 38 and the cover 40, respectively. The insulating layers 50, 52 may be made of one or more insulating materials, including Kapton® polyimide film, a product of E. I. du Pont de Nemours and Company of Wilmington, Del., U.S.A. ("DuPont"). The insulating layers 50, 52 are typically made from a flexible material. The material may be relatively less flexible than other layers of the flex circuit 22, and thus may actually increase the overall stiffness (i.e., may generally reduce the overall flexibility) of the flex circuit 22. In the flex circuit 22 embodiment illustrated in FIG. 3, the pad-side insulating layer 50 includes a cutout portion 78, and the cover-side insulating layer 52 includes a cutout portion 80. The cutout portions 78, 80 improve the flexibility of the insulating layers 50, 52, and thus improve the overall flexibility of the flex circuit 22. For example, if the end of the flex circuit 22 proximate the connector 44 is held in place, the opposing end of the flex circuit 22 may be rotated relative to the x-axis and the z-axis more easily than if the insulating layers 50, 52 did not include the cutout portions 78, 80. The improved flexibility helps to prevent inadvertent detachment of the NIRS sensor assembly 12 from the subject during operation. In the flex circuit 22 embodiment illustrated in FIG. 3, the pad-side insulating layer 50 includes a plurality of through-holes 82 for component wires to pass through for interconnection with the communication layer 48 of the flex circuit 22.

The pad-side shielding layer 54 and the cover-side shielding layer 56 are proximate (though not necessarily in contact with) the pad 38 and the cover 40, respectively. The pad-side shielding layer 54 and the cover-side shielding layer 56 each include a plurality of EMI shielding sheets that are preferably directly or indirectly connected to ground or another reference voltage, but not necessarily. As shown in FIG. 3, the pad-side shielding layer 54 includes: (1) an EMI shielding sheet 84 shaped to cover the near detector wires 58 and the EMI shielding wire 64 that circumscribes them; (2) an EMI shielding sheet 86 shaped to cover the far detector wires 60 and the EMI shielding wire 66 that circumscribes them; and (3) an EMI shielding sheet 88 shaped to cover the light detector wires 62 and the EMI shielding wire 68 that circumscribes them. Similarly, the cover-side shielding layer 56 includes: (1) an EMI shielding sheet 90 shaped to cover the near detector wires 58 and the EMI shielding wire 64 that circumscribes them; (2) an EMI shielding sheet 92 shaped to cover the far detector wires 60 and the EMI shielding wire 66 that circumscribes them; and (3) an EMI shielding sheet 94 shaped to cover the light detector wires 62 and the EMI shielding wire 68 that circumscribes them. The EMI shielding sheets 84, 86, 88, 90, 92, 94 of the shielding layers 54, 56 may be made from the same or similar material as the EMI shielding sheet 70 of the communication layer 48, or any other material operable to shield against EMI. In the flex circuit 22 embodiment illustrated in FIG. 3, the EMI shielding sheets 84, 86, 88 of the pad-side shielding layer 54 each include a plurality of through-holes 96 for components wires to pass through for interconnection with the communication layer 48 of the flex circuit 22.

Figure 7:
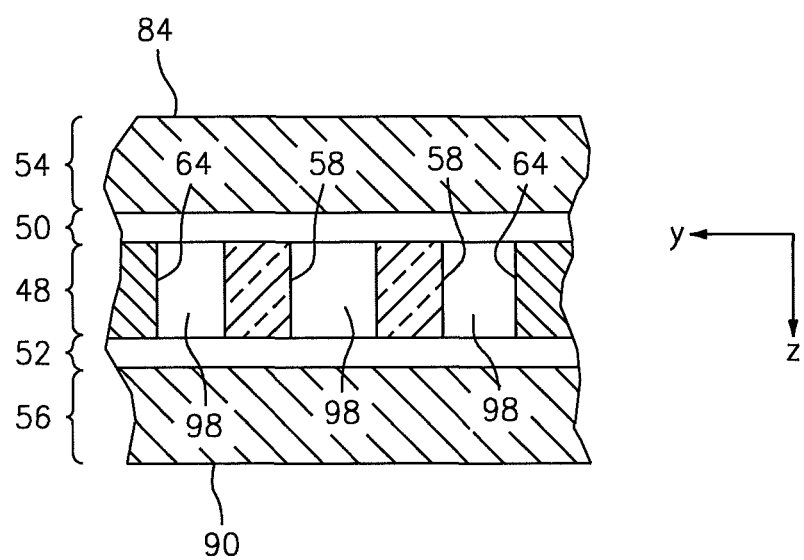
FIG. 7 a sectional view of the flexible electrical circuit embodiment illustrated in FIG. 3.
Figure 8:
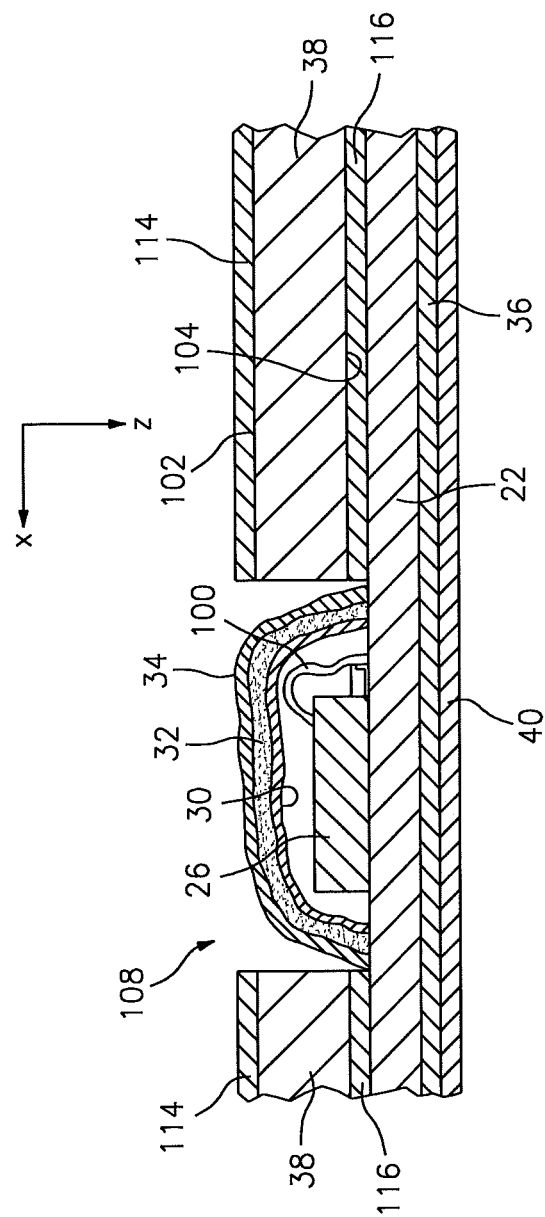
FIG. 8 is a sectional view of the NIRS sensor assembly shown in FIG. 2.

FIG. 7 illustrates a sectional view of the flex circuit 22 embodiment shown in FIGS. 3-6, including the communication layer 48, the pad-side insulating layer 50, the cover-side insulating layer 52, the pad-side shielding layer 54, and the cover-side shielding layer 56. The several layers of the flex circuit 22 are bonded or otherwise attached together to form a single structure, as discussed above. The two near detector wires 58 of the communication layer 48 are disposed between the EMI shielding wire 64. Cavities 98 separate the near detector wires 58 and the EMI shielding wire 64. The EMI shielding sheet 84 of the pad-side shielding layer 54 and the EMI shielding sheet 90 of the cover-side shielding layer 56 are disposed above and below the near detector wires 58, respectively. In viewing FIG. 7, it can be appreciated that the near detector wires 58 are surrounded by EMI shielding on four sides. Consequentially, the EMI shielding wire 64 and the EMI shielding sheets 84, 90 may be described as at least partially forming one or more Faraday Cages around the near detector wires 58. Although not shown in FIG. 7, Faraday Cages are similarly formed around the far detector wires 60 and the light source wires 62. Providing EMI shielding on four sides of the wires 58, 60, 62, as shown for example in FIG. 8, is advantageous for a number of reasons. First, as discussed above, the EMI shielding at least partially prevents cross-talk between the near detector wires 58, the far detector wires 60, and light source wires 62. Second, the near detector wires 58, the far detector wires 60, and light source wires 62 may be disposed in relative close proximity. Accordingly, the flex circuit 22 may be more compact and user friendly than would be possible otherwise.

Referring to FIGS. 2 and 8, a first insulating layer 30 is disposed relative to one or more of the light detectors 26, 28 in a manner that covers one or more exposed portions of the light detectors 26, 28. In some embodiments, including the embodiment illustrated in FIG. 2, the first insulating layer 30 may additionally be disposed relative to the light source 24 in a manner that covers one or more exposed portions of the light source 24. Referring to FIG. 2, portions of the light source 24 and the light detectors 26, 28 that are not directly attached to the flex circuit 22 are exposed. In some embodiments, the first insulating layer 30 may additionally cover one or more components of the NIRS sensor assembly 12 that are used to connect the light source 24 and/or the light detectors 26, 28 to the flex circuit 22. Referring to FIG. 8, for example, the first insulating layer 30 covers a wire 100 that electrically connects the near detector 26 to the flex circuit 22. The first insulating layer 30 prevents the wire 100 from contacting other electrically conductive components (e.g., EMI shielding layer 32) of the NIRS sensor assembly 12, and it provides an insulating barrier between the patient and the electrically conductive components of the NIRS sensor assembly 12. The first insulating layer 30 may include one continuous portion, or a plurality of independent portions. In FIG. 2, for example, the first insulating layer 30 includes three independent portions: a first portion 101 disposed relative to the light source 24, a second portion 103 disposed relative to the near detector 26, and a third portion 105 disposed relative to the far detector 28.

At least a portion of the first insulating layer 30 is optically transparent. In some embodiments, one or more portions of the first insulating layer 30 may be optically non-transparent. In such embodiments, one or more optically transparent portions of the first insulating layer 30 are disposed in alignment with the active regions of the light detectors 26, 28. In embodiments in which the first insulating layer 30 is disposed relative to the light source 24, one or more optically transparent portions of the first insulating layer 30 are disposed in alignment with the light source 24. For purposes of this description, the term "optically transparent" may be defined as follows: an optically transparent medium is one through which an amount of light may pass through, which amount is adequate for purposes of a NIRS evaluation. Conversely, an "optically non-transparent" medium is one that prevents passage of substantially all of light there through, which light would otherwise be available for a NIRS evaluation. The first insulating layer 30 is not limited to any particular material or combination of materials. In all embodiments, however, the first insulating layer 30 includes one or more materials that are electrically non-conductive, thereby making the first insulating layer 30 electrically non-conductive. Examples of acceptable materials that may be included in the first insulating layer 30 include: an ultraviolet curable epoxy (e.g., Loctite® 3525 epoxy made Henkel AG & Co. KGaA of Düsseldorf, Germany); or an electrically non-conductive film such as FEP tape made by DuPont. A significant advantage of the FEP tape is that it can be adhered in place during assembly, which greatly facilitates assembly.

An EMI shielding layer 32 is disposed in contact with the first insulating layer 30 in a manner that covers the first insulating layer 30. The EMI shielding layer 32 is preferably directly or indirectly connected to ground or another reference voltage, but not necessarily. The EMI shielding layer 32 may include one continuous portion, or a plurality of independent portions. In FIG. 2, for example, the EMI shielding layer 32 includes three independent portions: a first portion 107 disposed relative to the light source 24, a second portion 109 disposed relative to the near detector 26, and a third portion 111 disposed relative to the far detector 28. At least a portion of the EMI shielding layer 32 is optically transparent. In some embodiments, one or more portions of the EMI shielding layer 32 may be optically non-transparent. In such embodiments, an optically transparent portion of the EMI shielding layer 32 is disposed in alignment with the active regions of the light detectors 26, 28. In embodiments in which the EMI shielding layer 32 is disposed relative to the light source 24, one or more optically transparent portions of the EMI shielding layer 32 are disposed in alignment with the light source 24. The EMI shielding layer 32 is operable to reduce undesirable EMI-generated noise, and improves the signal to noise ratio of the light detectors 26, 28 (e.g., photodiodes). For example, the EMI shielding layer 32 may create one or more Faraday Cages around each of the light detectors 26, 28, while allowing light to reach the active regions of the light detectors 26, 28.

The EMI shielding layer 32 is not limited to any particular material or combination of materials. In all embodiments, however, the EMI shielding layer 32 includes one or more materials that are electrically conductive and operable to isotropically distribute EMI. In some embodiments, the one or more optically transparent portions of the EMI shielding layer 32 may include an electrically conductive wire mesh (e.g., copper wire mesh), or may include an electrically conductive substrate. An example of such an electrically conductive substrate is a fiber-filled, conductive adhesive tape such as XYZ-Axis Electrically Conductive Tape 9713, offered by 3M Company of St. Paul, Minn., U.S.A (referred to hereinafter as "9713 Tape"). The electrically conductive substrate (e.g., 9713 Tape) may contain electrically conductive fibers that allow for isotropic distribution of EMI. The electrically conductive substrate can come in a double-sided form that has adhesive on both sides. An electrically conductive substrate provides several advantages, including: (1) it is relatively inexpensive; (2) it does not require a soldered connection to ground; (3) it is available in roll form; (4) it has a low profile; and (5) it is flexible. In embodiments in which a portion of the EMI shielding layer 32 is optically non-transparent, the one or more optically non-transparent portions may include an electrically conductive metal foil, such as a copper metal foil. An electrically conductive gasket, such as silicone paste, adhesive, foam, or other similar material, may be used to create an electrical interface between the optically transparent portion and optically non-transparent portion of the EMI shielding layer 32, particularly in those embodiments that utilize a wire mesh as the optically non-transparent portion.

The second insulating layer 34 is disposed in contact with the EMI shielding layer 32 in a manner that covers the EMI shielding layer 32 and the first insulating layer 30. The second insulating layer 34 provides a further insulating barrier between the patient and the electrically conductive components of the NIRS sensor assembly 12 (e.g., EMI shielding layer 32). The second insulating layer 34 may include one continuous portion, or a plurality of independent portions. In FIG. 2, for example, the second insulating layer 34 includes three independent portions: a first portion 113 disposed relative to the light source 24, a second portion 115 disposed relative to the near detector 26, and a third portion 117 disposed relative to the far detector 28. At least a portion of the second insulating layer 34 is optically transparent. In some embodiments, one or more portions of the second insulating layer 34 may be optically non-transparent. In such embodiments, an optically transparent portion of the second insulating layer 34 is disposed in alignment with the active regions of the light detectors 26, 28. In embodiments in which the second insulating layer 34 is disposed relative to the light source 24, one or more optically transparent portions of the second insulating layer 34 are disposed in alignment with the light source 24. The second insulating layer 34 need not be made of any particular material or combination of materials. In all embodiments, however, the second insulating layer 34 includes one or more materials that are electrically non-conductive, thereby making the second insulating layer 34 electrically non-conductive. The third insulating layer 36 may be made of the same materials or different materials than the first insulating layer 30.

A third insulating layer 36 may be disposed on the side of the flex circuit 22 proximate the cover 40. The third insulating layer 36 may include one continuous portion, or a plurality of independent portions. In FIG. 2, for example, the third insulating layer 36 includes one continuous portion having a geometry that generally matches the geometry of the pad 38. The third insulating layer 36 is shaped and positioned on the NIRS sensor assembly 12 so that the flex circuit 22 is disposed between the third insulating layer 36 and the pad 38. The third insulating layer 36 is not limited to any particular material or combination of materials. In all embodiments, however, the third insulating layer 36 includes one or more materials that are electrically non-conductive. The third insulating layer 36 may be made of the same materials or different materials than the first insulating layer 30 and the second insulating layer 34.

The above-described structure (e.g., the stack up of the flex circuit 22, the light source 24, the light detectors 26, 28, the first insulating layer 30, the EMI shielding layer 32, and the second insulating layer 34) provides a structure that allows light signals to be sensed, and at the same time reduces undesirable EMI generated noise and improves the signal to noise ratio of the light detectors 26, 28. During use of the NIRS sensor assembly 12, a percentage of the light signal produced by the light source 24 passes through the biological tissue of the patient, then through the first insulating layer 30, the EMI shielding layer 32, and the second insulating layer 34, after which it is sensed by the light detectors 26, 28. At the same time, the EMI shielding layer 32 attenuates local EMI that may be present.

Referring to FIG. 2, the pad 38 has a patient-side surface 102, a component-side surface 104, one or more light source apertures 106, and one or more light detector apertures 108, 110. The light detector apertures 108, 110 are each shaped to receive at least a portion of the light detectors 26 and 28, respectively. The light source aperture 106 is shaped to receive at least a portion of the light source 24. The light detector apertures 108, 110 and light source aperture 106 are typically aligned along a center line 112 of the pad 38. The pad 38 is preferably made from a flexible material (e.g., foam) that is optically non-transparent. Poron® cellular urethane foam, a product of Rogers Corporation of Woodstock, Conn., U.S.A., is an example of an acceptable pad 38 material. As shown in FIG. 8, an adhesive 114 may be applied to the patient-side surface 102 for attaching the pad 38 to the subject, and an adhesive 116 may be applied to the component-side surface 104 for attaching the pad 38 to the flex circuit 22.

Referring to FIGS. 2 and 8, the cover 40 is positioned on the NIRS sensor assembly 12 so that the flex circuit 22 is disposed between the cover 40 and the pad 38. The geometry of the cover 40 can vary. In FIG. 2, the geometry of the cover 40 generally matches the geometry of the pad 38. The cover 40 is not limited to any particular material or combination of materials. The cover 40 is preferably a soft pliable material that can be used in a patient environment. Tyvek®, a product made by DuPont, is an example of an acceptable cover 40 material. Other acceptable materials include vinyl materials, plastic materials, and foam materials (e.g., Poron®). The cover 40 may be attached to the NIRS sensor assembly 12 in a variety of different ways; e.g., by adhesive, mechanical features, etc. The cover 40 material preferably blocks light from entering the NIRS sensor assembly 12. The cover 40 may be molded, cast or formed in place to create a tailored fit.

Referring to FIG. 2, the tail cover 42 includes a top portion 118 and a bottom portion 120. The top portion 118 of the tail cover 42 is disposed on the same side of the NIRS sensor assembly 12 as the pad 40. The bottom portion 120 of the tail cover 42 is disposed on the same side of the NIRS sensor assembly 12 as the cover 40. The top and bottom portions 118, 120 of the tail cover 42 are preferably flexible and operable to protect the flex circuit 22 disposed there between. The top and bottom portions 118, 120 are attached to one another to enclose a portion of the flex circuit 22. The top and bottom portions 118, 120 may be made of one or combination of known laminates.

The connector 44 is configured to provide electrical/signal communication directly, or indirectly, between the NIRS sensor assembly 12 and the base unit 14. The present NIRS system 10 is not limited to use with any particular connector 40. Examples of acceptable connectors are disclosed in International Patent Application No. PCT/US12/24889, which is incorporated by reference in its entirety hereinabove, and in U.S. Provisional Patent Application No. 61/717,401, which is hereby incorporated by reference in its entirety.

In the operation of the present invention, once the NIRS sensor assembly 12 is positioned relative to the subject's skin, it may be actuated and light signals introduced into the subject's body tissue. The light introduced into the subject's body tissue is subsequently detected using the light detectors 26, 28 producing signals representative of such detected light. The signals are relayed back to the base unit 14, where they are processed to obtain data relating to a characteristic of the subject's biological tissue; e.g., to obtain data relating to the blood oxygenation level of the subject's biological tissue.

Since many changes and variations of the disclosed embodiment of the invention may be made without departing from the inventive concept, it is not intended to limit the invention otherwise than as required by the appended claims. For example, the present invention is disclosed in the context of a cerebral application. The present invention is not limited to cerebral oximetry applications and can be used for non-invasive monitoring of blood oxygenation levels in other body tissues and fluids.

What is claimed is:

1. A near-infrared spectroscopy (NIRS) sensor assembly for measurement of a characteristic of a biological tissue, the NIRS sensor assembly comprising:
   a flexible electrical circuit;
   at least one light source operable to emit light signals, which at least one light source is in electrical communication with the flexible electrical circuit, and which at least one light source has an attached portion and a remaining portion of the at least one light source that is exposed, which attached portion is attached to the flexible electrical circuit;
   at least one light detector operable to detect light signals emitted by the light source, the at least one light detector having an active area through which light signals may be detected, which at least one light detector is in electrical communication with the flexible electrical circuit, and which at least one light detector has an attached portion and a remaining portion of the at least one light detector that is exposed, which attached portion is attached to the flexible electrical circuit;
   a first insulating layer disposed to enclose the exposed portion of the at least one light detector on the flexible electrical circuit, wherein the first insulating layer is electrically non-conductive, and wherein an optically transparent portion of the first electrical insulating layer is aligned with the active area of the at least one light detector,
   an electromagnetic interference (EMI) shielding layer disposed in contact with the first insulating layer and covering the first insulating layer, wherein the EMI shielding layer is electrically conductive, and wherein an optically transparent portion of the EMI shielding layer is aligned with the active area of the at least one light detector;
   a second insulating layer disposed in contact with the EMI shielding layer and covering the EMI shielding layer and the first insulating layer, wherein the second insulating layer is electrically non-conductive, and wherein an optically transparent portion of the second insulating layer is aligned with the active area of the at least one light detector; and
   a sensor connector in electrical communication with the flexible electrical circuit.

2. The NIRS sensor assembly of claim 1, wherein the first insulating layer includes an electrically non-conductive tape.

3. The NIRS sensor assembly of claim 1, wherein the EMI shielding layer includes a fiber-filled, electrically conductive substrate.

4. The NIRS sensor assembly of claim 1, wherein the second insulating layer includes an electrically non-conductive tape.

5. The NIRS sensor assembly of claim 1, wherein the flexible electrical circuit includes a plurality of light source wires configured to communicate electrical signals between the at least one light source and a connector portion of the NIRS sensor assembly.

6. The NIRS sensor assembly of claim 5, wherein the flexible electrical circuit further includes at least one EMI shielding wire disposed relative to the plurality of light source wires so that the at least one EMI shielding wire at least partially defines a Faraday Cage around the plurality of light source wires.

7. The NIRS sensor assembly of claim 1, wherein the flexible electrical circuit includes a plurality of light detector wires configured to communicate electrical signals between the at least one light detector and the connector portion.

8. The NIRS sensor assembly of claim 7, wherein the flexible electrical circuit further includes at least one EMI shielding wire disposed relative to the plurality of light detector wires so that the at least one EMI shielding wire at least partially defines a Faraday Cage around the plurality of light detector wires.

9. The NIRS sensor assembly of claim 1, wherein the flexible electrical circuit comprises a communication layer, a first circuit insulating layer extending between the at least one light source, the at least one light detector, and the sensor connector, a second circuit insulating layer extending between the at least one light source, the at least one light detector, and the sensor connector, a first circuit shielding layer extending between the at least one light source, the at least one light detector, and the sensor connector, and a second circuit shielding layer extending between the at least one light source, the at least one light detector, and the sensor connector, wherein the first circuit insulating layer is disposed between the first circuit shielding layer and a first side of the communication layer, and wherein the second circuit insulating layer is disposed between the second circuit shielding layer and an opposing second side of the communication layer.

10. The NIRS sensor assembly of claim 9, wherein the first circuit insulating layer is electrically non-conductive and provides a barrier between the communication layer and the first circuit shielding layer, and wherein the second circuit insulating layer is electrically non-conductive and provides a barrier between the communication layer and the second circuit insulating layer.

11. The NIRS sensor assembly of claim 9, wherein the first circuit shielding layer includes at least one EMI shielding sheet, and wherein the second circuit shielding layer includes at least one EMI shielding sheet.

12. The NIRS sensor assembly of claim 11, wherein the communication layer of the flexible electrical circuit includes a plurality of light source wires configured to communicate electrical signals between the at least one light source and a connector portion of the NIRS sensor assembly, wherein the communication layer includes at least one EMI shielding wire disposed relative to the plurality of light source wires, and wherein the at least one EMI shielding wire, the at least one EMI shielding sheet of the first circuit shielding layer, and the at least one EMI shielding sheet of the second circuit shielding layer at least partially define a Faraday Cage around the plurality of light source wires.

13. The NIRS sensor assembly of claim 11, wherein the communication layer of the flexible electrical circuit includes a plurality of light detector wires configured to communicate electrical signals between the at least one light detector and a connector portion of the NIRS sensor assembly, wherein the communication layer includes at least one EMI shielding wire disposed relative to the plurality of light detector wires, and wherein the at least one EMI shielding wire, the at least one EMI shielding sheet of the first circuit shielding layer, and the at least one EMI shielding sheet of the second circuit shielding layer at least partially define a Faraday Cage around the plurality of light detector wires.

14. The NIRS sensor assembly of claim 1, wherein the flexible electrical circuit includes a plurality of light source wires configured to communicate electrical signals between the at least one light source and a connector portion of the NIRS sensor assembly, wherein the flexible electrical circuit includes a plurality of light detector wires configured to communicate electrical signals between the at least one light detector and a connector portion of the NIRS sensor assembly, and wherein the flexible electrical circuit includes EMI shielding configured to at least partially prevent cross-talk between the plurality of light source wires and the plurality of light detector wires.

15. The NIRS sensor assembly of claim 1, further comprising a third insulating layer disposed in contact with the flexible electrical circuit on a side of the flexible electrical circuit opposite the at least one light source and the at least one light detector.

16. The NIRS sensor assembly of claim 1, further comprising:
a pad having a light source aperture and a light detector aperture, wherein the at least one light source is received at least partially within the light source aperture, wherein the at least one light detector is at least partially received within the light detector aperture, and wherein the pad is positioned within the NIRS sensor assembly to contact a subject during operation of the NIRS sensor assembly.

* * * * *